(12) United States Patent
Takeshita

(10) Patent No.: US 7,683,244 B2
(45) Date of Patent: Mar. 23, 2010

(54) **INTERSPECIFIC HYBRID OF *LOBELIA* AND METHOD OF PRODUCING THE SAME**

(75) Inventor: Daigaku Takeshita, Tochigi (JP)

(73) Assignee: Kirin Agribio Company, Limited, Tokyo (JP)

( * ) Notice: Subject to any disclaimer, the term of this patent is extended or adjusted under 35 U.S.C. 154(b) by 408 days.

(21) Appl. No.: 11/389,037

(22) Filed: Mar. 27, 2006

(65) Prior Publication Data

US 2006/0218678 A1 Sep. 28, 2006

(30) Foreign Application Priority Data

Mar. 28, 2005 (JP) ............... 2005-091303

(51) Int. Cl.
*A01H 5/00* (2006.01)
*A01H 1/00* (2006.01)
*A01H 5/02* (2006.01)

(52) U.S. Cl. .................. 800/323; 800/298; 800/295; 800/260; 435/419; 435/431

(58) Field of Classification Search ................. None
See application file for complete search history.

(56) References Cited

U.S. PATENT DOCUMENTS

| PP10,758 | P | 1/1999 | Westhoff |
| PP12,536 | P2 | 4/2002 | Trees |
| PP13,264 | P2 | 11/2002 | Heims |
| 2002/0092044 | A1 | 7/2002 | Trees |
| 2004/0139518 | P1 | 7/2004 | Oud |

*Primary Examiner*—Medina A Ibrahim
(74) *Attorney, Agent, or Firm*—Stephen A. Bent; Foley & Lardner LLP

(57) ABSTRACT

An object of the present invention is to develop a novel *Lobelia* plant and a breeding method thereof, which allow for first-filial-generation (F1) hybrids exhibiting morphological forms (having the advantages of their two parents and far exceeding the traits of the two parents) desired by their breeder. The present invention thus provides a novel *Lobelia* plant by crossing *Lobelia richardsonii* (seed parent) and *Lobelia valida* (pollen parent), which while being a hybrid in first-filial-generation (F1) population of the genetically stable wild species, nevertheless the F1 population exhibits an even distribution over a range from a hybrid close to the seed parent to a hybrid close to the pollen parent.

5 Claims, 8 Drawing Sheets
(8 of 8 Drawing Sheet(s) Filed in Color)

F1 hybrids

*erinus*

(Azuro® compact sky blue)      No.63

No. 77

INTERSPECIFIC HYBRID OF *LOBELIA* AND METHOD OF PRODUCING THE SAME

FIELD OF THE INVENTION

The present invention relates to novel interspecific first-filial-generation (F1) hybrids of *Lobelia* of genetically stable wild species, wherein the F1 hybrids vary largely in their characteristics and exhibit an even distribution over a range from a hybrid close to the seed parent to a hybrid close to the pollen parent. The present invention also relates to a method of producing the novel interspecific hybrids of *Lobelia*. Moreover, the present invention relates to a variety of cells, tissues, or organs of the hybrids, such as pollen, ovules, seeds, and cuttings, and to later generation thereof

BACKGROUND OF THE INVENTION

First-filial-generation (F1) hybrids of genetically stable wild species are generally population with high genetic and morphological uniformity. Many interspecific cross combinations even within the same genus fail to produce hybrids, and therefore the cross compatibility can be determined only by actually practicing the cross. Ovule or embryo culture is in practical use as a method for breaking cross incompatibility barriers. However, only some interspecific combinations can provide hybrids even by this technique, and unless the culture is actually performed, whether hybrids can successfully be produced can not be judged under present circumstances.

Especially, F1 hybrids between wild species are population with high genetic and morphological uniformity and therefore, are less likely to include F1 hybrids exhibiting morphological forms (having the advantage of their both parents and far exceeding the traits of the both parents) desired by their breeder.

The genus *Lobelia* includes approximately 375 species with diverse properties such as annual, perennial, shrubby, woody properties, and most of them are native to tropical and warm-temperate regions.

Although there exist some interspecific cross combinations within the genus *Lobelia* that successfully produce hybrids (see Patent Documents 1 to 3), it has not been reported so far that reciprocal crossing between *Lobelia richardsonii* and *Lobelia valida* produces hybrids. All interspecific hybrids of *Lobelia* previously produced have been obtained only by traditional crossing. Thus, no report has described hybrids produced by the combination of cross and ovule culture.

[Patent Document 1]: U.S. Plant Pat. No. 10,758
[Patent Document 2]: U.S. Patent Publication No. 20020092044 A1
[Patent Document 3]: U.S. Plant Pat. No. 12,536

*Lobelia valida* (wild species) is tolerant of high temperatures and however, exhibits a poorly balanced and upright form. Moreover, it has a disadvantage of being less apt to become a large plant (plant bearing stems creeping sideways with thick, rising branching). Therefore, the breeding of *Lobelia valida* varieties that become large well-balanced plants has been desired.

On the other hand, *Lobelia richardsonii* (wild species) is tolerant of high temperatures and however, exhibits a fully trailing form. Besides, it has disadvantages of having very short flowering time because of its exceedingly strong long-day flowering habit and of less blooming. Therefore, the breeding of *Lobelia richardsonii* varieties that continually flower and profusely bloom has been demanded.

Thus, an object of the present invention is to find out a combination of two parents that gives F1 hybrids exhibiting an even distribution over a range from a hybrid close to the pollen parent to a hybrid close to the seed parent and possessing heat tolerance, and to breed a desired F1 hybrid therefrom.

SUMMARY OF THE INVENTION

The present inventors have conducted studies for attaining the object, and have consequently found out that the selection of *Lobelia richardsonii* as a seed parent and *Lobelia valida* as a pollen parent from among various interspecific cross combinations provides for first-filial-generation (F1) hybrids of the genetically stable wild species, wherein the F1 hybrids exhibit an even distribution over a range from a hybrid close to the seed parent to a hybrid close to the pollen parent and also possess heat tolerance. Of the obtained F1 hybrids, all four lines defined by deposition Nos described below became lager than the pollen parent and grew faster and bloomed longer than the seed parent. Moreover, these four lines continually flowered from spring to fall. Two lines (deposition Nos. FERM BP-10287 and FERM BP-10288) that produce large flowers, profusely bloom (produce numerous flowers), and become large plants could be obtained from the four lines.

Moreover, the present inventors have found out that ovule culture after crossing can prevent hybrid embryos from withering and produce hybrids more efficiently.

Namely, the present invention provides a novel *Lobelia* plant, which is a hybrid in first-filial-generation (F1) population obtained by crossing of genetically stable wild species *Lobelia richardsonii* (seed parent) and *Lobelia valida* (pollen parent), wherein the F1 population exhibits an even distribution over a range from a hybrid close to the seed parent to a hybrid close to the pollen parent.

A preferable example of the plant can include a *Lobelia* plant identified as deposition No. FERM BP-10301, FERM BP-10287, FERM BP-10288, or FERM BP-10302.

The present invention also provides a part of the *Lobelia* plant according to the present invention, that is, a cell, tissue, or organ of the plant, such as pollen, ovules, seeds, and cuttings, as well as a culture of the cell, tissue, or organ.

The present invention also provides a later generation of the *Lobelia* plant according to the present invention.

Furthermore, the present invention provides a method of producing the novel *Lobelia* plant according to the present invention. The method comprises the steps of 1) crossing *Lobelia richardsonii* (seed parent) and *Lobelia valida* (pollen parent) and 2) culturing a swollen ovule extracted from the resulting swollen ovary after crossing to obtain a plant.

The novel *Lobelia* plant obtained by the method may further be crossed with any of other *Lobelia* plants known in the art in order to obtain a later generation. For example, the F1 plants can be crossed by self-pollination or cross-pollination to breed another novel *Lobelia* plant.

The present invention has demonstrated a case showing wide-ranging diversity in F1 hybrids between the genetically stable wild species. As a result, crossing between wild species within the genus *Lobelia* that is expected to produce diverse F1 hybrids will be practiced more actively.

The novel *Lobelia* plant obtained in the present invention is a hybrid, which is in first-filial-generation (F1) population that exhibits an even distribution over a range from a hybrid close to the seed parent to a hybrid close to the pollen parent and also possesses heat tolerance. Therefore, the novel *Lobelia* plant of the present invention is capable of cultivation in periods and situations in which conventional varieties are impossible to cultivate. As a result, the market expansion of *Lobelia* plants can be expected.

BRIEF DESCRIPTION OF THE DRAWINGS

The patent or Application filed contains at least one drawing executed in color. Copies of this patent or patent Application publication with color drawing(s) will be provided by the Office upon request and payment of the necessary fee.

DETAILED DESCRIPTION OF THE PREFERRED EMBODIMENTS

Figure 1:
FIG. 1 is a photograph showing a large variety of F1 hybrids between *Lobelia richardsonii* (seed parent)×*Lobelia valida* (pollen parent)
Figure 2:
FIG. 2 is a photograph of No. 22 (growth and blooming in a pot)
Figure 3:
FIG. 3 is a photograph of comparison among No. 26 (center) and its two parents *valida* (right) and *richardsonii* (left)
Figure 4:
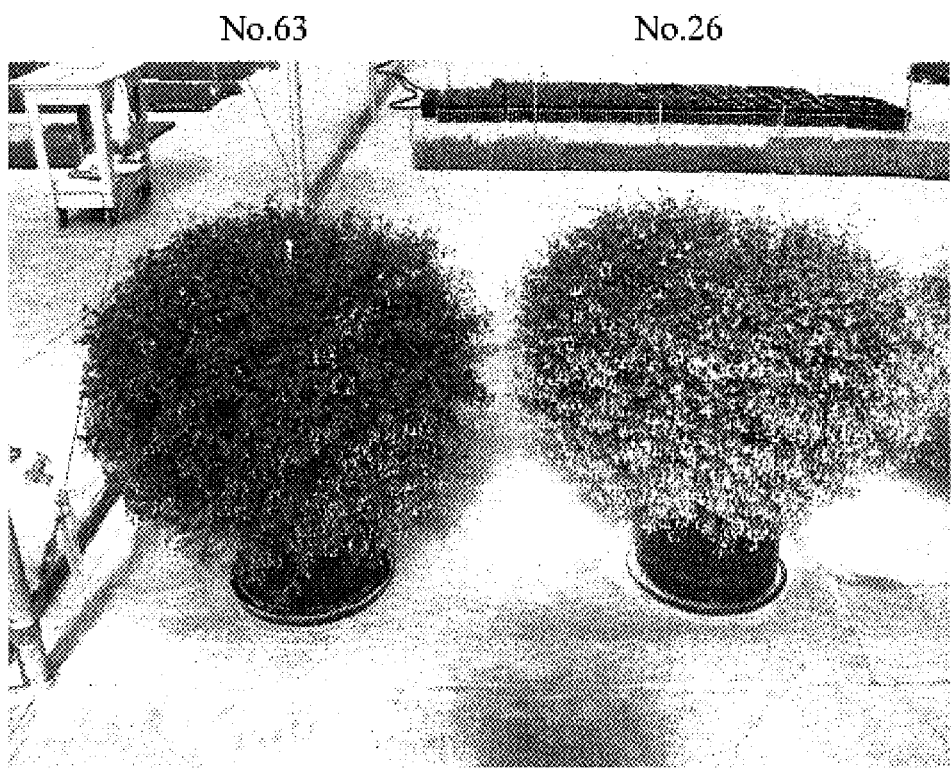
FIG. 4 is a photograph of No. 26 (right) and No. 63 (left)
Figure 5:
FIG. 5 is a photograph of comparison between No. 26 (right) and *erinus* (Regatta sky blue) (left)
Figure 6:
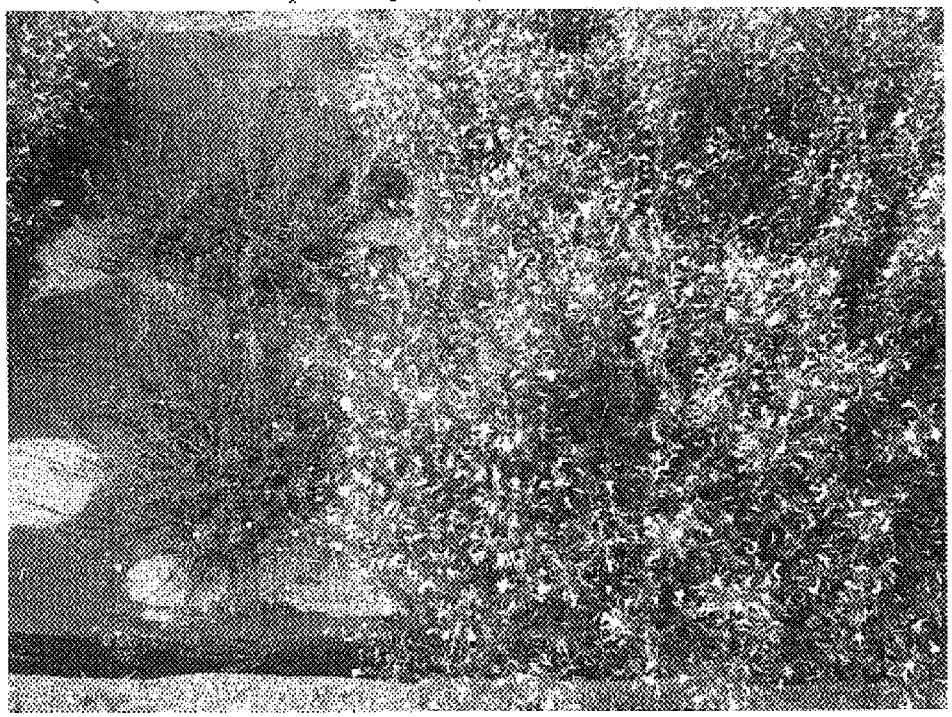
FIG. 6 is a photograph of comparison between the performances of No. 63 (right) and *erinus* (Azuro® compact sky blue) (left) in filed cultivation.
Figure 7:
FIG. 7 is a photograph showing the size of No. 63.
Figure 8:
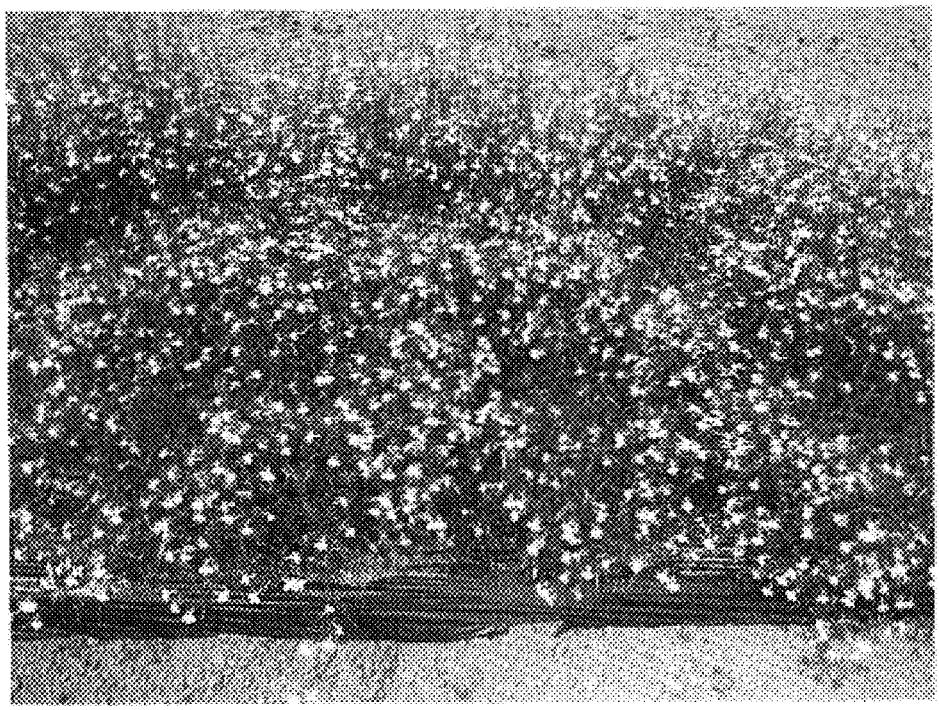
FIG. 8 is a photograph of No. 77 (growth and blooming in a field).

Hereinafter, the present invention will be described in detail.

1. Novel *Lobelia* Plant

A "novel *Lobelia* plant" according to the present invention is a novel plant belonging to the genus *Lobelia* obtained by crossing between *Lobelia richardsonii* used as a seed parent and *Lobelia valida* used as a pollen parent. The "novel *Lobelia* plant" of the present invention is a hybrid in first-filial-generation (F1) population of the genetically stable wild species, nevertheless the F1 population exhibits an even distribution over a range from a hybrid morphologically close to the seed parent to a hybrid morphologically close to the pollen parent and possesses heat tolerance. Therefore, the "novel *Lobelia* plant" of the present invention neither stops its growth nor withers in a high-temperature period (at air temperature in a greenhouse during the day in midsummer of Japan, i.e., approximately 30 to 40° C.).

Preferably, the "novel *Lobelia* plant" of the present invention possesses properties of becoming larger than the pollen parent, growing faster and blooming longer than the seed parent, and continually flowering from spring to fall.

More preferably, the "novel *Lobelia* plant" of the present invention possesses properties of producing large flowers, profusely blooming (producing numerous flowers), and becoming a large plant. In this context, the phrase "becoming a large plant" or "becoming large" means that a plant width (diameter of the whole plant likened to a circle) is not smaller than 60 cm, preferably not smaller than 80 cm, more preferably not smaller than 1 m. The "large flowers" mean that the diameter of the flower is approximately 20 mm to 40 mm. The phrase "profusely blooming" means that the number of flowers per plant is 100 to 500, preferably 200 to 500, more preferably 300 to 500.

The "novel *Lobelia* plant" of the present invention can representatively be exemplified by lines No. 22, No. 26, No. 63, and No. 77. No. 26 is a line having a form close to that of the seed parent; No. 63 is a line having an intermediate form slightly close to that of the seed parent; No. 77 is a line having an intermediate form slightly close to that of the pollen parent; and No. 22 is a line having a form close to that of the pollen parent. The characteristics of these lines are as shown in Table 1.

The calluses of the No. 22, No. 26, No. 63, and No. 77 are internationally deposited as deposition Nos. FERM BP-10301 (deposited on Mar. 23, 2005), FERM BP-10287 (deposited on Mar. 4, 2005), FERM BP-10288 (deposited on Mar. 4, 2005), and FERM BP-10302 (deposited on Mar. 23, 2005), respectively, in International Patent Organism Depositary, National Institute of Advanced Industrial Science and Technology (Tsukuba Central 6, 1-1-1 Higashi, Tsukuba, Ibaraki, Japan).

The scope of the present invention encompasses a part of the "novel *Lobelia* plant" of the present invention, that is, a cell, tissue, or organ thereof. The cell, tissue, or organ encompasses all cells, tissues, or organs at every stage of differentiation of the plant. Namely, the cell may be a single cell or cell population (cell mass) and includes protoplast and spheroplast. Likewise, the tissue may be a single tissue or tissue population and includes every type of tissue such as phloem (e.g., epidermal tissue, parenchyma, sieve tube, and phloem fiber) and xylem (e.g., vessel, tracheid, and xylem fiber). Alternatively, the organ includes every type of organ such as stems, tubers, leaves, roots, tuberous roots, cuttings, floral buds, flowers, petals, pistils, stamens, anthers, pollen, ovaries, fruits, pods, capsules, seeds, fibers, ovules, and embryos.

In a preferred embodiment, the cell, tissue, or organ is in a regenerable state and is provided as a culture obtained from cell, tissue, or organ culture. Examples of such a culture can include a culture of a shoot apex, a culture of an axillary bud-containing node, a culture of a stem or stem slice, a culture of a leaf or leaf slice, a culture of a root or root slice, and a culture of a petal. The plant of the present invention can be regenerated from the culture according to a routine method.

Cell or tissue culture allows for large-scale propagation of plants by using a cell or tissue from a region with high cell division activity such as the shoot apex of a bud, an axillary bud, or a dormant bud under appropriately determined environmental conditions, and as such, is useful as a plant propagation method that replaces seed reproduction and vegetative reproduction.

For example, a method as described below may be used as such a propagation method. Nodal segments containing one axillary bud are cut from plants maintained in a field or greenhouse and can be grown by transplanting them to the commercially available nursery soils.

Alternatively, the nodal segments containing one axillary bud are sterilized according to a sterilization method for swollen ovaries described in Example 1 below, and then plated in a plant tissue culture medium (selected without particular limitations from typical plant tissue culture media such as MS medium, White medium, and Nitsch medium) as described in the paragraph 2 below. At the point of time when new axillary buds are formed from the elongated nodes (usually after approximately 4 weeks from the planting), nodal segments containing one axillary bud are cut from the nodes and plated in a medium of the same composition. Propagation can be achieved by repeating these procedures of node elongation and plating. The plant tissue culture medium can be prepared according to a method known in the art. Any of the typical plant tissue culture media is usually supplemented with any one of or any appropriate combination of 0.1 to 6% (by weight), preferably 1 to 4% (by weight), sucrose, glucose, and fructose serving as a sugar source. After the pH adjustment of the medium to 5 to 6, preferably 5.6 to 5.8, the medium is further supplemented with agar (0.4 to 1.2%, preferably 0.6 to 1.0%, by weight) or gellan gum (0.1 to 0.4%, preferably 0.15 to 0.25%, by weight) serving as a solidifying agent. Then, the resulting medium is autoclaved (e.g., at 121° C. for 15 min) and can thereby be prepared as the plant tissue culture medium that can be used in the present invention. In this case, a plant growth regulator such as auxin and cytokinin is not particularly required to be added before the addition of the solidifying agent. However, the use of, for example, a variety of cytokinins (e.g., zeatin, 6-benzyladenine, and kinetin) and gibberellic acids such as $GA_3$ alone or in appropriate combination sometimes further promotes growth (node elongation). A liquid medium in addition to a solid medium is also available as this growth medium. Although culture conditions are not particularly limited, culture at 20 to 30° C. for 12- to 20-hour day length under illumination of 400 to 6500 lux is typically preferred. More preferably, culture conditions at 25±2° C. for 16-hour day length under illumination of 600 to 2000 lux can be selected.

2. Method of Producing Novel *Lobelia* plant

The "novel *Lobelia* plant" of the present invention can be produced by crossing *Lobelia richardsonii* used as a seed parent and *Lobelia valida* used as a pollen parent. It is preferred to perform ovule culture (Wakizuka, T. and Nakajima, T., 1974, Jpn. J. Breed., 24: 182-187) after crossing, in order to prevent hybrid embryos from withering and obtain hybrids more efficiently.

For example, swollen ovules are extracted from the resulting swollen ovaries after approximately 7 to 10 days from the crossing and sterilized according to a routine method. The ovules are aseptically cultured on a medium. The medium used in this ovule culture is selected without particular limitations from media typically used in plant tissue culture such as MS medium, White medium, and Nitsch medium. Although culture conditions are not particularly limited, culture at 20 to 30° C. for 12- to 20-hour day length under illumination of 400 to 6500 lux is typically preferred. For example, culture conditions at 25±2° C. for 16-hour day length under illumination of 600 to 2000 lux can be selected.

Seedlings can be obtained after approximately 1.5 to 2 months from the ovule culture. The seedlings are acclimatized in commercially available nursery soils (e.g., Sunshine Mix; manufactured by Sungro Horticulture) in a greenhouse. Then, the seedlings are potted and raised, and can thereby be allowed to bloom. The obtained F1 plants exhibit an even distribution over a range from a hybrid morphologically close to the seed parent to a hybrid morphologically close to the pollen parent. Therefore, an interspecific hybrid having a desired trait can be selected therefrom.

The obtained F1 plant may further be crossed with any of other *Lobelia* plants. For example, the obtained F1 plants can be crossed by self-pollination to fix the trait. Alternatively, the obtained F1 plant can be crossed with the F1 plant having a different trait by cross-pollination to obtain another novel *Lobelia* plant.

Once the "novel *Lobelia* plant" according to the present invention is obtained, a part of the plant such as seeds, stems, leaves, and roots (vegetative reproduction such as grafting and division) or a culture thereof can be used to obtain a later generation (progeny) of the plant according to a routine method. The scope of the present invention also encompasses such a later generation. Methods known in the art such as naturally-occurring or artificial mutation, cell fusion, and gene recombination can be used alone or in appropriate combination as an alternative method for obtaining the later generation.

EXAMPLES

Hereinafter, the present invention will be described more fully with reference to Reference Example and Examples. However, the present invention is not intended to be limited to them.

Reference Example

*Lobelia richardsonii* used in Examples below was a commercially available variety named Monet. The genetic stability of this variety was confirmed by the following procedures: nodal segments containing one axillary bud were cut from plants maintained in a field or greenhouse as described above and were grown by transplanting them to the commercially available nursery soils (Sunshine Mix; manufactured by Sungro Horticulture); plural nodes containing plural axillary buds were obtained therefrom and cut into nodal segments containing one axillary bud; these nodal segments were propagated; the confirmation that all of 100 plants obtained from further raising and 50 later-generation plants produced by self-fertilization of the variety had almost the same characteristics as that of the variety and exhibited excellent uniformity was performed Example 1

Reciprocal crossing between *Lobelia richardsonii* (commercially available variety named Monet) and *Lobelia valida* (commercially available variety) was performed. As a result, no swollen ovary was observed in the crossing between *Lobelia valida* used as a seed parent and *Lobelia richardsonii* used as a pollen parent, whereas swollen ovaries were confirmed to be produced on rare occasion from the crossing between *Lobelia richardsonii* used as a seed parent and *Lobelia valida* used as a pollen parent.

The swollen ovaries were incised, and their interior regions were examined. Consequently, one to two swollen ovules per ovary were present in the swollen ovaries. Most of the swollen ovaries were observed to wither after a certain time, before the seeds attained full maturity. Therefore, the swollen ovules extracted from the swollen ovaries after 7 to 10 days from the crossing were cultured by an ovule culture method. Namely, the swollen ovaries after 7 to 10 days from the crossing were transferred to a clean bench and sterilized by immersing the swollen ovaries in a beaker containing 70% ethanol solution for approximately 10 seconds and subsequently in a sodium hypochlorite solution of 0.5% available chlorine concentration for approximately 7 minutes. The resulting swollen ovaries were well rinsed with sterile water and further wiped dry with a sterilized filter paper. Approximately 200 ovules were cut from the sterilized swollen ovaries using a scalpel under a light microscope and plated in an autoclaved (at 121° C. and 1 atm) medium (adjusted to pH 5.8) of Murashige and Skoog's (MS) inorganic salt formulation (Murashige and Skoog, Plant Physiol. 15: 473-497, 1962) supplemented with 3% by weight of sucrose as a sugar source and further with gibberellin ($GA_3$) (adjusted to 100 ppm) and solidified with 0.8% agar (manufactured by Wako). The resulting ovules were cultured in a culture chamber (illumination of 700 lux, 16-hour day length, temperature of 25±2° C.). After approximately 1.5 to 2 months, 86 seedlings of approximately 2 cm were obtained.

The obtained seedlings were sequentially acclimatized in soils for raising cell seedlings in a greenhouse (20 to 25° C., natural day length). Then, the seedlings were potted and raised, and thereby allowed to bloom. Therefore, the characteristics of a total of 86 hybrids were investigated.

As a result, the morphological forms of the obtained F1 plants exceeded the degree deduced from usual F1 population and were immensely rich in diversity. Namely, the F1 plants exhibit serial morphological forms from an plant having a form close to that of *Lobelia richardsonii* (variety name: Monet) serving as a seed parent to a hybrid having a form close to that of *Lobelia valida* serving as a pollen parent (FIG. 1). The breakdown of the occurrence (ratio) was 25 hybrids (29.1%; containing No. 26) morphologically close to the seed parent, 39 intermediate hybrids (45.3%; containing No. 63) morphologically slightly close to the seed parent, 14 intermediate hybrids (16.3%; containing No. 77) morphologically slightly close to the pollen parent, and eight hybrids (9.3%; containing No. 22) morphologically close to the pollen parent.

These F1 plants were confirmed to be true interspecific hybrids by the measurement of their growth state and by morphological observation during flowering time.

The calluses of the No. 22, No. 26, No. 63, and No. 77 are internationally deposited as deposition Nos. FERM BP-10301 (deposited on Mar. 23, 2005), FERM BP-10287 (deposited on Mar. 4, 2005), FERM BP-10288 (deposited on Mar. 4, 2005), and FERM BP-10302 (deposited on Mar. 23, 2005), respectively, in International Patent Organism Depositary, National Institute of Advanced Industrial Science and Technology (Tsukuba Central 6, 1-1-1 Higashi, Tsukuba, Ibaraki, Japan).

Consequently, F1 hybrids having traits desired by the breeder were not limited to one type but there could be selected plural F1 hybrids that exhibited evidently different morphological forms such as hybrids close to the seed parent (large, fully trailing plants), intermediate hybrids slightly close to the seed parent (semi-trailing plants: large plants with fully-trailing primary branches but plagiotropic secondary branches), intermediate hybrids slightly close to the pollen parent (semi-trailing, bushy plants), and hybrids close to the pollen parent (upright plants that do not become large). Although the obtained hybrids included those having traits intended by the breeder (hybrids that produce numerous flowers and become large plants) and those not having the traits (hybrids that neither become large nor produce numerous flowers or hybrids that become large but produce no flower because of their floral buds withering immediately before flowering), all of them basically exhibited excellent heat tolerance.

Most of the hybrids did not possess pollen fertility. However, approximately 20% of the hybrids (17 hybrids) produced pollen. The breakdown of the 17 hybrids was two hybrids (No. 31 and No. 55) close to the seed parent, four intermediate hybrids (No. 12, No. 37, No. 40, and No. 51) slightly close to the seed parent, seven intermediate hybrids (No. 11, No. 17, No. 21, No. 45, No. 59, No. 77, and No. 78) slightly close to the pollen parent, and four hybrids (No. 2, No. 22, No. 72, and No. 79) close to the pollen parent. When the self-pollination of these hybrids was performed, some of them were confirmed to normally produce seeds. The breakdown thereof was one hybrid (No. 55) close to the seed parent, three intermediate hybrids (No. 37, No. 40, and No. 51) slightly close to the seed parent, four intermediate hybrids (No. 21, No. 45, No. 59, and No. 77) slightly close to the pollen parent, and three hybrids (No. 22, No. 72, and No. 79) close to the pollen parent.

Example 2

Grafted seedlings were raised from selected hybrids of two lines (10 to 20 hybrids per line) close to the pollen parent, nine intermediate lines (10 to 20 hybrids per line) slightly close to the pollen parent, 6 intermediate lines (10 to 20 hybrids per line) slightly close to the seed parent, and 6 lines (10 to 20 hybrids per line) close to the seed parent, obtained in Example 1 above. These grafted seedlings were planted in the field of Plant Laboratory, Kirin Brewery Co. Ltd., together with their two parents one *Lobelia richardsonii* line (variety name: Monet; 10 plants) and 1 *Lobelia valida* line (10 plants) as well as two *Lobelia erinus* varieties (see Table 1; 10 plants each), to practice the comparative test of their characteristics. The obtained result of the comparative test was similar to the result of evaluating seedlings obtained in the ovule culture, in the greenhouse. Moreover, the obtained F1 hybrids neither stopped their growth nor withered in a high-temperature period, and had excellent heat tolerance. Data about the characteristics of arbitrary one hybrid each from the F1 lines and the commercially available *Lobelia* lines are shown in Table 1, and photographs of the F1 lines are shown in FIGS. 2 to 8.

TABLE 1

Comparative data of *Lobelia*

| | (Crossed) species name<br>Line name (characteristic) | | | |
|---|---|---|---|---|
| | *richardsonii* × *valida*<br>No. 22 (close to pollen parent) | *richardsonii* × *valida*<br>No. 26 (close to seed parent) | *richardsonii* × *valida*<br>No. 63 (intermediate slightly close to seed parent) | *richardsonii* ×*valida*<br>No. 77 (intermediate slightly close to pollen parent) |
| Plant habit | Upright | Fully trailing | Semi-trailing | Semi-trailing/bush |
| Plant height | 40 cm | 15 cm | 30 cm | 40 cm |
| Plant width | 35 cm | Over 1 m | Over 1 m | 80 cm |
| Stem color | Green | Purple | Purplish green | Purplish green |
| Stem thickness | 6 mm | 3 mm | 3 mm | 4 mm |
| Internode length | 8 mm | 7 mm | 5 mm | 5 mm |
| Upper leaf shape | Inferior | Inferior | Inferior | Inferior |
| Upper leaf size | 24 mm × 5 mm | 19 mm × 5 mm | 19 mm × 5 mm | 22 mm × 5 mm |
| Degree of serration of upper leaf | Present, slight | Present, slight | Present, slight | Present, slight |
| Lower leaf shape | Ovate | Ovate | Ovate | Ovate |
| Lower leaf size | 32 mm × 25 mm | 32 mm × 21 mm | 36 mm × 21 mm | 34 mm × 21 mm |
| Degree of serration of lower leaf | Present | Present | Present | Present |

TABLE 1-continued

Comparative data of *Lobelia*

| | | | | |
|---|---|---|---|---|
| Leaf color: front face | Green: RHS color chart 131C | Green: RHS color chart 133A | Green: RHS color chart 132B | Green: RHS color chart 132B |
| Leaf color: back face | Green: RHS color chart 131C | Purple: RHS color chart N79B | Slightly purplish green | Slightly purplish green |
| Flowering habit | Long-day flowering habit | Week long-day flowering habit | Week long-day flowering habit | Week long-day flowering habit |
| Floral bud length | 13 mm | 13 mm | 13 mm | 13 mm |
| Flower size | 22 mm × 22 mm | 22 mm × 22 mm | 22 mm × 22 mm | 22 mm × 22 mm |
| The number of petal: upper petal | 2 | 2 | 2 | 2 |
| The number of petal: lower petal | 3 | 3 | 3 | 3 |
| Petal size: upper petal | 8 mm × 3 mm | 8 mm × 3 mm | 8 mm × 3 mm | 8 mm × 3 mm |
| Petal size: lower petal | 13 mm × 6 cm | 13 mm × 6 cm | 13 mm × 6 cm | 13 mm × 6 cm |
| Petal color: upper petal | RHS color chart 98A | RHS color chart 98A | RHS color chart 98A | RHS color chart 98A |
| Petal color: lower petal | RHS color chart 98A | RHS color chart 98A | RHS color chart 98A | RHS color chart 98A |
| Pedicel length | 15 mm | 30 mm | 30 mm | 25 mm |
| Ovary size | 3 mm × 3 mm | 2 mm × 3 mm | 2 mm × 3 mm | 2 mm × 3 mm |
| Anther color | Light blue: RHS color chart 100D | Light blue: RHS color chart 100D | Light blue: RHS color chart 100D | Light blue: RHS color chart 100D |
| Pistil length | 9 mm | 9 mm | 9 mm | 9 mm |
| Pistil color | Purple: RHS color chart N89A | Purple: RHS color chart N89A | Purple: RHS color chart N89A | Purple: RHS color chart N89A |

| | Species name (Variety name) | | | |
|---|---|---|---|---|
| | *valida* | *richardsonii* (Monet) | *erinus* Azuro ® compact sky blue, Syngenta) (Laguna sky blue; Syngenta) | *erinus* (Regatta sky blue; Pan American seed) |
| Plant habit | Upright | Fully trailing | Bush | Semi-trailing |
| Plant height | 40 cm | 5 cm | 20 cm | 10 cm |
| Plant width | 30 cm | Over 1 m | 60 cm | 40 cm |
| Stem color | Green: | Purple: | | |
| Stem thickness | 6 mm | 3 mm | 3 mm | 2 mm |
| Internode length | 8 mm | 10 mm | 4 mm | 4 mm |
| Upper leaf shape | Inferior | Inferior | Inferior | Inferior |
| Upper leaf size | 26 mm × 6 mm | 18 mm × 4 mm | 18 mm × 4 mm | 18 mm × 4 mm |
| Degree of serration of upper leaf | Present, slight | Absent | Absent | Absent |
| Lower leaf shape | Ovate | Obovate | Ovate | Ovate |
| Lower leaf size | 32 mm × 17 mm | 28 mm × 18 mm | 25 mm × 13 mm | 25 mm × 13 mm |
| Degree of serration of lower leaf | Present | Present | Present | Present |
| Leaf color: front face | Green: RHS color chart 131C | Green: RHS color chart 133A | Green: RHS color chart 132C | |
| Leaf color: back face | Green: RHS color chart 131C | Purple: RHS color chart N79B | Green: RHS color chart 132C | |
| Flowering habit | Long-day flowering habit | Strong long-day flowering habit | Nearly perpetual flowering habit | Perpetual flowering habit |
| Floral bud length | 13 mm | 13 mm | 11 mm | 10 mm |
| Flower size | 22 mm × 22 mm | 22 mm × 22 mm | 18 mm × 19 mm | 17 mm × 18 mm |
| The number of petal: upper petal | 2 | 2 | 2 | 2 |
| The number of petal: lower petal | 3 | 3 | 3 | 3 |
| Petal size: upper petal | 8 mm × 3 mm | 4 mm × 2 mm | 4 mm × 2 mm | 4 mm × 2 mm |
| Petal size: lower petal | 13 mm × 6 cm | 10 mm × 6 mm | 9 mm × 6 mm | 8 mm × 6 mm |
| Petal color: upper petal | RHS color chart 96C | RHS color chart 100C | RHS color chart 100A | |
| Petal color: lower petal | RHS color chart 96C | RHS color chart 100C | RHS color chart 100A | |
| Pedicel length | 11 mm | 30 mm | 19 mm | 18 mm |
| Ovary size | 3 mm × 3 mm | 2 mm × 3 mm | 2 mm × 3 mm | 2 mm × 3 mm |
| Anther color | Light blue: RHS color chart 100D | Light blue: RHS color chart 100D | Light blue: RHS color chart 100D | Light blue: RHS color chart 100D |
| Pistil length | 9 mm | 9 mm | 7 mm | 7 mm |
| Pistil color | Purple: RHS color chart N89A | Purple: RHS color chart N89A | Purple: RHS color chart N89A | Purple: RHS color chart N89A |

Comparative Example 1

The production of interspecific hybrids in the following 12 combinations of the species *speciosa, erinus, richardsonii, sessilifolia,* and *valida* was attempted according to Example 1 and however, was unsuccessful:

1) *speciosa* (seed parent)×*erinus* (pollen parent);
2) *erinus* (seed parent)×*speciosa* (pollen parent);
3) *speciosa* (seed parent)×*richardsonii* (pollen parent);
4) *richardsonii* (seed parent)×*speciosa* (pollen parent);
5) *sessilifolia* (seed parent)×*erinus* (pollen parent);
6) *erinus* (seed parent)×*sessilifolia* (pollen parent);
7) *sessilifolia* (seed parent)×*richardsonii* (pollen parent);
8) *richardsonii* (seed parent)×*sessilifolia* (pollen parent);
9) *valida* (seed parent)×*speciosa* (pollen parent);
10) *speciosa* (seed parent)×*valida* (pollen parent);
11) *valida* (seed parent)×*sessilifolia* (pollen parent); and
12) *sessilifolia* (seed parent)×*valida* (pollen parent).

INDUSTRIAL APPLICABILITY

The hybrids obtained in the present invention have the advantages of their two parents (*Lobelia richardsonii* and *Lobelia valida*) and far exceed the traits of the two parents. Namely, the hybrids obtained in the present invention exhibit an even distribution over a range from a hybrid close to the seed parent to a hybrid close to the pollen parent and also possess heat tolerance. Therefore, the hybrids of the present invention are capable of cultivation in periods and situations in which conventional varieties are impossible to cultivate. As a result, the market expansion of *Lobelia* plants can be expected.

What is claimed is:

1. A *Lobelia* plant, that is a hybrid in first-filial-generation (F1) population obtained by
   a) crossing a genetically stable wild species *Lobelia richardsonii* (seed parent) and *Lobelia valida* (pollen parent), which crossing results in a swollen ovary in the seed parent;
   b) culturing a swollen ovule extracted from the swollen ovary to obtain a F1 plant; and
   c) repeating steps a) and b) to obtain the F1 population, whereby the F1 population exhibits an even distribution of morphological characteristics over a range from a hybrid close to the seed parent to a hybrid close to the pollen parent.

2. The plant according to claim 1, wherein the plant is identified as deposition No. FERM BP-10301, FERM BP-10287, FERM BP-10288, or FERM BP-10302.

3. A culture of a cell, tissue, or organ of the plant according to claim 1.

4. A method of producing a *Lobelia* plant that is a hybrid in first-filial-generation (F1) population, said method comprising:
   a) crossing a genetically stable wild species *Lobelia richardsonii* (seed parent) and *Lobelia valida* (pollen parent), which crossing results in a swollen ovary in the seed parent;
   b) culturing a swollen ovule extracted from the swollen ovary to obtain a F1 plant; and
   c) repeating steps a) and b) to obtain the F1 population, whereby the F1 population exhibits an even distribution of morphological characteristics over a range from a hybrid close to the seed parent to a hybrid close to the pollen parent.

5. The method according to claim 4, further comprising the step of selecting a plant with a desired trait from obtained F1 hybrids.

* * * * *